United States Patent [19]

Kuroda et al.

[11] Patent Number: 5,490,193
[45] Date of Patent: Feb. 6, 1996

[54] X-RAY COMPUTED TOMOGRAPHY SYSTEM

[75] Inventors: Katsuhiro Kuroda, Hachioji; Koichi Koike, Kashiwa; Atsuko Takafuji, Tokyo; Fumio Noda, Hachioji, all of Japan

[73] Assignees: Hitachi, Ltd.; Hitachi Medical Corporation, both of Tokyo, Japan

[21] Appl. No.: 734,168

[22] Filed: Jul. 22, 1991

[30] Foreign Application Priority Data

Jul. 23, 1990 [JP] Japan ................................ 2-192943

[51] Int. Cl.⁶ .................................................. H05G 1/60
[52] U.S. Cl. ............................ 378/10; 378/9; 378/16
[58] Field of Search ............................ 378/10, 9, 16

[56] References Cited

U.S. PATENT DOCUMENTS

| | | | |
|---|---|---|---|
| 4,672,649 | 6/1987 | Rutt | 378/10 |
| 4,866,745 | 9/1989 | Akai | 378/137 |

FOREIGN PATENT DOCUMENTS

2044985  10/1980  United Kingdom ................ 378/137

Primary Examiner—Craig E. Church
Attorney, Agent, or Firm—Antonelli, Terry, Stout & Kraus

[57] ABSTRACT

This invention provides a compact X-ray CT system capable of obtaining an X-ray CT image having high resolution at a high speed by deflecting a predetermined electron beam and causing the finely focused electron beam to scan on an arcuate anode target inside the same plane as the arcuate anode target for an X-ray source. The anode target for an X-ray source and a detector are disposed in the form of arcs inside substantially the same plane so as to face each other. The electron beam emitted from an electron gun is guided to a deflector through a lens system, is then deflected to a arc form trajectory by a uniform magnetic field generated by the deflector and is guided to the anode target after a reverse magnetic field is applied to the electron beam at a desired position. This electron beam is caused to scan on the anode target at a high speed so as to move the generation position of the X-ray and thus to obtain a sectional image.

32 Claims, 11 Drawing Sheets

X-RAY COMPUTED TOMOGRAPHY SYSTEM

BACKGROUND OF THE INVENTION

This invention relates to an X-ray computed tomography system (hereinafter referred to as an "X-ray CT system"). More particularly, the present invention relates to a system for obtaining a sectional image of an object the image of which is to be taken by irradiating an X-ray to the object, detecting the quantity of the transmitted X-ray, processing the detected signal by a computer or the like, and obtaining the sectional image, and specifically to the structure of an X-ray scanner for constituting the part which irradiates the X-ray to the object the image of which is to be taken, and detects the quantity of the transmitted X-ray.

In order to obtain a sectional image of an object the image of which is to be taken, an X-ray CT system needs an X-ray scanner which irradiates the X-rays to the object from a plurality of directions around the object and detects signals. The X-ray scanner in X-ray CT systems for medical diagnosis which has been used most widely at present disposes an X-ray source and a detector so as to face each other in an arc form and obtains signals from the peripheral direction of the object the image of which is to be taken, by rotating them unitarily and mechanically. (Refer, for example, to JP-B-1-45594.) Since the X-ray scanner is rotated mechanically, however, a rotating speed exceeding one turn per second cannot be obtained. Accordingly, dynamic imaging such as the motion of the heart, for example, cannot be made.

Figure 16:
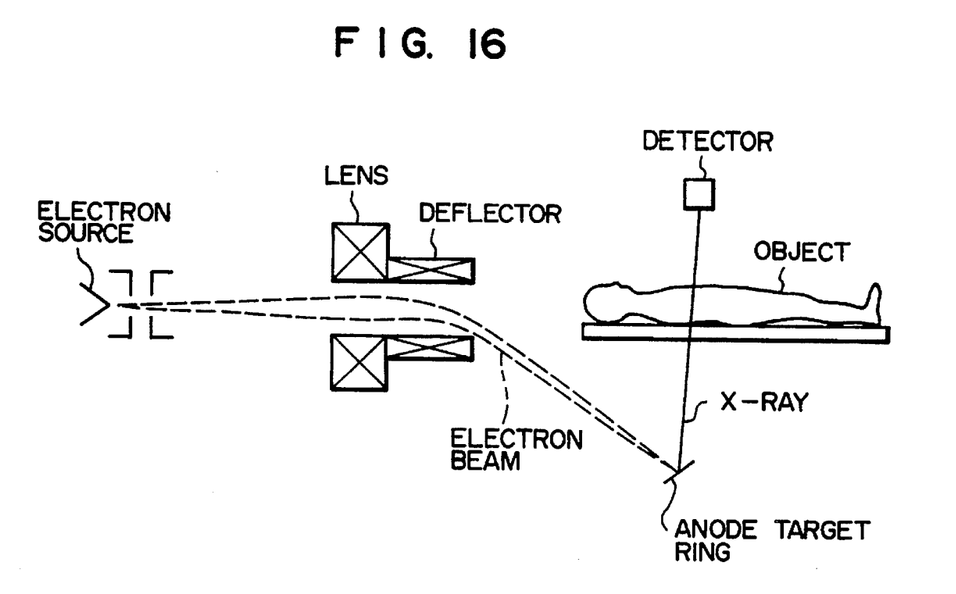
FIG. 16 is a schematic view of a conventional X-ray CT system.

In order to solve this problem, an X-ray scanner which rotates electrically the X-ray source such as the one shown in FIG. 16 has been proposed (JP-A-60-12656). An anode target ring for the X-ray source and a plurality of detectors are shaped in the form of an arc and are fixed in such a manner as to face one another, an electron beam source is disposed at the apex of a cone using this circle has the bottom surface and an electron beam is scanned on the anode target ring for the X-ray source by deflection means so as to rotate the X-ray source. For this reason, mechanical rotation is not required. As a prior-art apparatus for similarly effecting high speed rotation, JP-A-61-68032 describes a method which deflects an electron beam in a circular trajectory inside a plane which is parallel to the sectional plane and irradiates the electron beam to an anode target ring for an X-ray source by a magnetic field.

SUMMARY OF THE INVENTION

The prior-art apparatus described above does not give much consideration to how to reduce the scale of the apparatus and to obtain an X-ray CT image having high resolution. More specifically, the prior-art apparatus constitutes large scale means for deflecting the electron beam to a circular trajectory and then irradiating the beam to the anode target ring for the X-ray source by the combination of a deflection coil with a deflection yoke or the combination of an electrostatic deflection electrode with a deflection yoke and so on. In connection with means for obtaining an X-ray CT image having high resolution, the prior-art does not consider at all a method of guiding the electron beam from the electron beam source to the circular trajectory, the X-ray generation position and the electron beam in the circular trajectory.

With the technical background described above, the present invention is therefore directed to provide an X-ray CT system which solves the problems with the prior art, which is compact in scale, and which obtains an X-ray CT image having high resolution at a high speed.

First of all, to accomplish the object described above, the electron beam is deflected to a circular trajectory inside substantially the same plane as the arcuate anode target for the X-ray source and is allowed to scan on the anode target. In this instance, if two electron sources are provided, the object can be accomplished at higher degree. If means for deflecting the electron beam in the arc form and means for causing the electron beam to scan on the anode target are provided, the electron beam is allowed to scan on the anode target and these two means can be accomplished by the same deflection means. In order to keep constant the diameter of the electron beam to be irradiated to the anode target for the X-ray source, lens means capable of adjusting the diameter of the electron beam and its focusing angle is necessary. When the electron beams from the electron sources are incident into the arc form trajectory, they must be incident from a field-free state to a uniform magnetic field. Therefore, an arrangement is employed so that the electron beams pass through a pipe which is shielded magnetically. Furthermore, electron beam focusing means for preventing the divergence of the electron beams due to the space charge effect inside the arc form trajectory is added in order to accomplish higher resolution. The construction described above can accomplish an X-ray CT system which is compact in scale, provides high resolution and can take an image at a high speed.

When the electron beam is deflected and is caused to scan on the anode target for the X-ray source in the arc form, the position of the X-ray source is rotated electrically when speaking equivalently, and high speed imaging becomes possible. Next, the X-ray scanner which occupies the major capacity of the X-ray CT system can be made compact in scale if the rotating plane of the electron beam is on the same plane as the anode target for the X-ray source. Furthermore, if two electron sources are provided, these electron sources can be selected in accordance with the X-ray generation position and the diameter of the electron beam to be irradiated to the anode target can be reduced, so that high resolution can be accomplished. If two electron sources are provided, the travelling distance of the electron beam can be reduced and the apparatus can be made compact in scale by reducing the dimension of the lens system.

Furthermore, the apparatus can be made compact in scale by constituting both means for deflecting the electron beam in the arc form and means for causing the electron beam to scan in the arc form on the anode target by the same means. If lens means for adjusting the diameter of the electron beam and its focusing angle in accordance with the X-ray generation position is provided, scanning can be effected while the diameter of the electron beam on the anode target is kept constant at a value as small as possible, and high resolution can thus be accomplished.

When the electron beam is allowed to be incident into the uniform magnetic field through the pipe which is shielded magnetically, the trajectory of the electron beam is guided from a straight line to an arc at a certain point, so that deflection accuracy can be improved and high resolution can be accomplished.

High resolution can be accomplished also by providing means for focusing the electron beam.

The present invention is completed on the basis of the principle described above, and provides a system which is compact in scale and can provide an X-ray CT image having high resolution at a high speed.

DESCRIPTION OF THE PREFERRED EMBODIMENTS

Hereinafter, some preferred embodiments of the present invention will be described.

Figure 1:
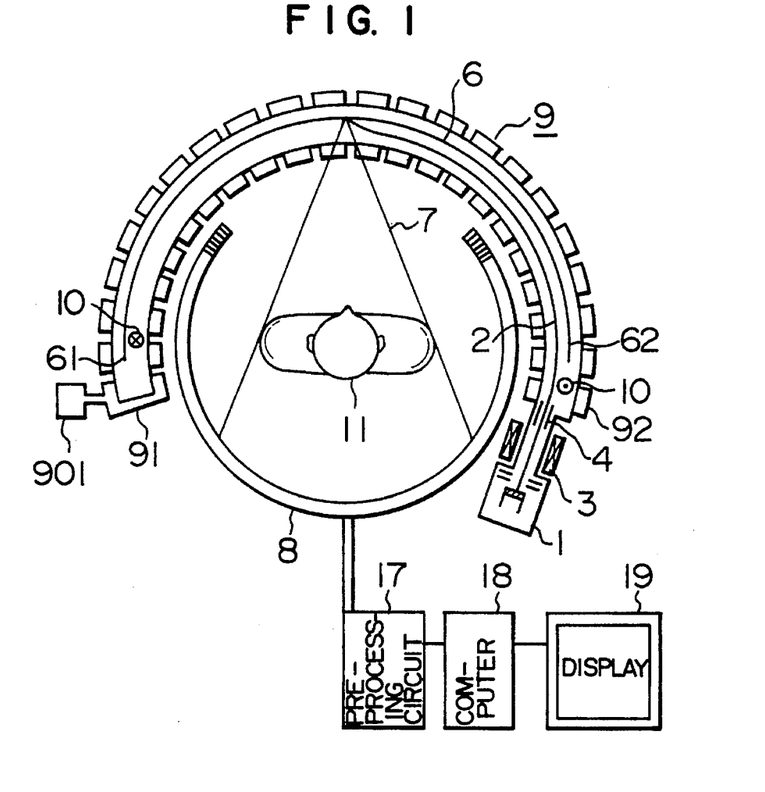
FIG. 1 is a sectional plan view of a system of the present invention.
Figure 2:
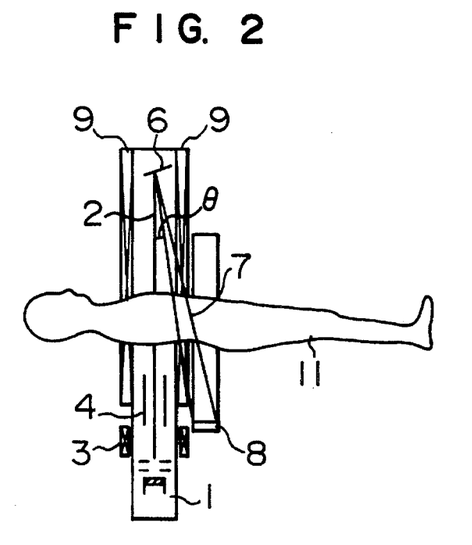
FIG. 2 is a sectional side view of the system of the present invention.

FIGS. 1 and 2 are a sectional plan view and a sectional side view of an X-ray CT system in accordance with the present invention, particularly its X-ray scanner part.

An anode target 6 for an X-ray source is shaped in the form of an arc. A diverging electron beam 2 emitted from an electron gun 1 as the electron source is adjusted by a lens system 3. This electron beam 2 is projected into a uniform magnetic field 10 (with the direction of the magnetic field extending from the back to the face of the sheet of drawings) generated by a magnetic deflector 9, and takes an arc form trajectory. In this case, however, an arrangement is employed so that the electron beam 2 passes through a pipe 4, which is shielded magnetically, up to a range in which a uniform magnetic field necessary for the electron beam 2 to take a substantially arc form trajectory is provided. For, since the anode target 6 as the generation position of the X-ray must be constituted in the form of an arc, the electron beam, too, must take a substantially arc form trajectory. The plane of the arc form trajectory of the electron beam 2 and the plane in which the arcuate anode target 6 is contained are substantially the same plane. Here, the direction of a current to be passed through deflectors is reversed at a certain position between a magnetic deflector 91 and a deflector 92 and hence, the electron beam 2 on the arc form trajectory is deflected and irradiates the anode target 6 for the X-ray source. The X-rays 7 generated by the anode target 6 irradiate an object 11, the image of which is to be taken, such as a patient, and the transmitted X-rays are detected by a plurality of detectors 8 arranged in such a manner as to face the anode target 6, and are converted to electric signals. These detectors 8 are disposed in the plane which is substantially the same as the plane containing the anode target 6 in the arc form (the X-rays 7 incident into the detectors 8 describing an angle $\phi$ of up to 20° with the plane containing the arcuate anode target 6). Here, if the magnetic deflector 9 is operated in time sequence from the deflector 91 to the deflector 92, the irradiation target position of the electron beam 2 or in other words, the X-ray generation position, too, is scanned from the anode target position 61 to the anode target position 62. The X-rays emitted from each anode target position transmit through the object 11 whose image is to be taken, and are detected as electric signals by the detector 8 made of a plurality of detection elements.

The subsequent procedures are the same as those of a heretofore known X-ray CT system. The electric signal is filtered by a pre-processing circuit 17 and subjected to processing such as A/D conversion, and a computer 18 executes signal processing such as the generation of a sectional image. The resulting image is displayed as the sectional image by a display 19. Incidentally, in the drawings illustrating the embodiments of the invention, the pre-processing circuit, the computer and the display are omitted.

Figure 3A:
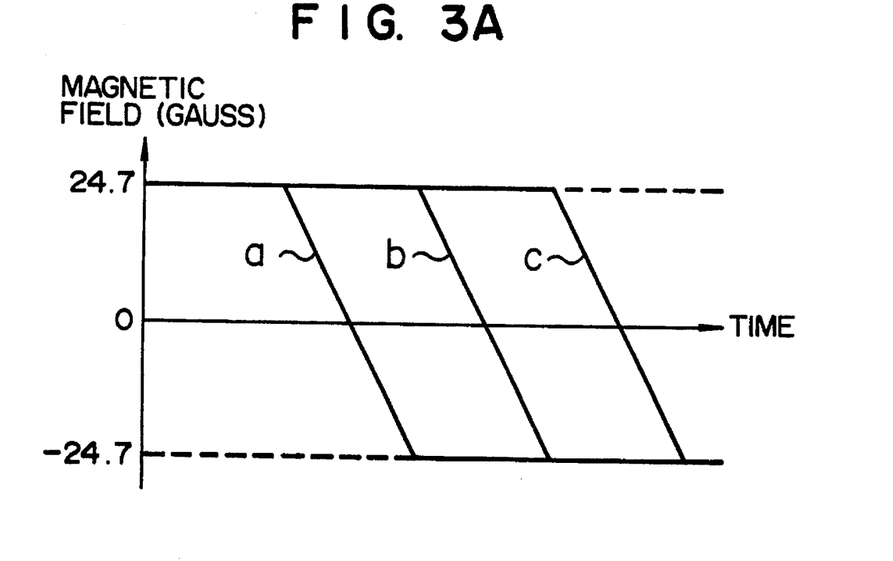
FIG. 3A is a characteristic diagram of a deflector used for the system of the present invention.
Figure 3B:
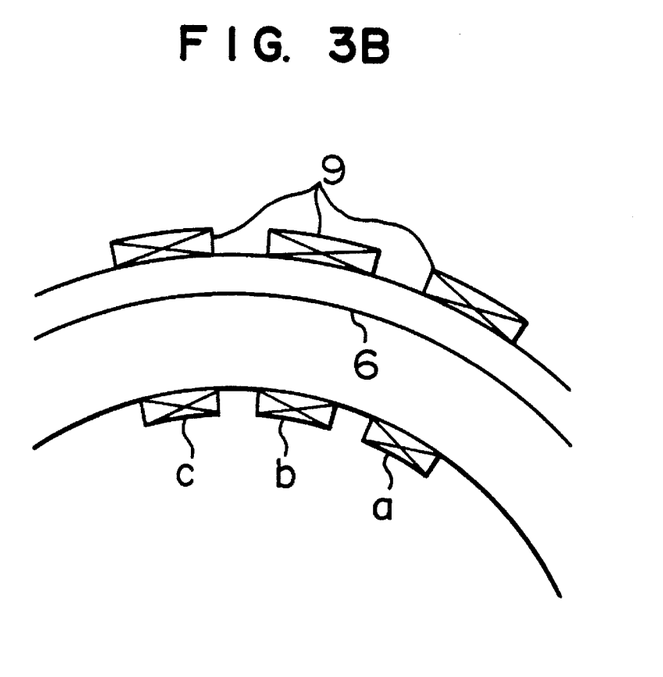
FIG. 3B is a structural view of the deflector.

An electron beam of a current value of 1 A and a cross-over of about 0.3 mm$\phi$ is obtained at an accelerating voltage of 120 kV by the electron gun 1 using LaB$_6$ (lanthanum hexaboride). This electron beam describes an arc form trajectory having a radius of about 50 cm in a uniform magnetic field of 24.7 Gauss. Each of the magnetic deflectors 91 to 92 uses a coil of about 200 ampere·turn. The diameter of the electron beam at this time is about 1 mm and X-rays having an effective value of energy of about 70 keV are obtained from the anode target 6. The range of at least 180° from the anode target position 61 to the anode target position 62 describes an arc and the range from the magnetic deflectors 91 to 92 comprises 24 deflecting coils. Therefore, the current to be passed through each deflector shown in FIG. 3B is reversed in the shape of the teeth of a saw in a predetermined time interval so as to generate the magnetic field having the shape of the teeth of a saw as shown in FIG. 3A, so that the electron beam 2 is deflected to the arc form trajectory and is irradiated to the anode target 6 to make continuous scanning. Though a power supply 901 for the magnetic deflector is shown disposed only for the deflector 91 in FIG. 1, such power supplies are of course added to the other deflectors. In the drawings showing the later-appearing embodiments, these power supplies for the deflectors are omitted. The magnetic deflector 9 of the embodiment shown in FIG. 1 may comprise a coil which is formed by rolling in multiple the deflectors 91 to 92 on one magnetic field generation coil having the form of an arc embracing therein the arc of the anode target 6. On the other hand, the detector 8 is constituted by arranging about 500 detectors within the range of an arc having a radius of about 40 cm and a center angle of about 220°.

Figure 4:
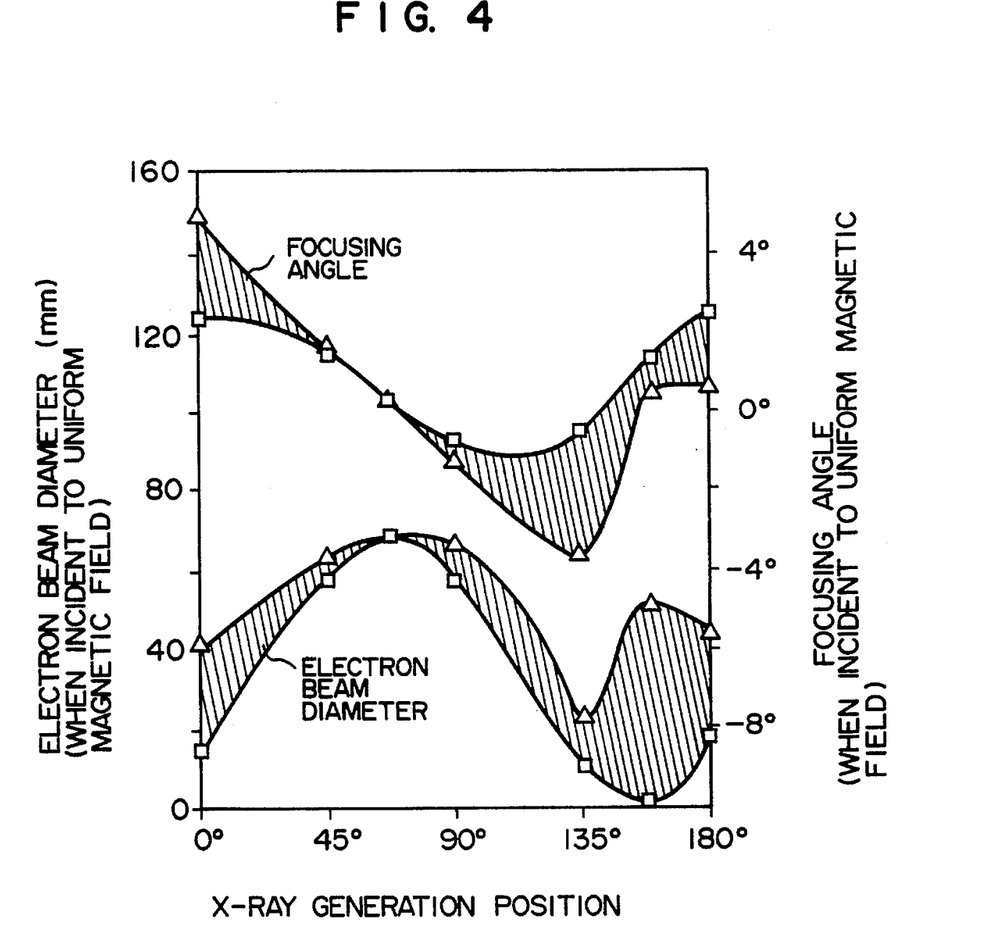
FIG. 4 is a characteristic diagram of an electron beam in a scanning direction in the present invention.
Figure 5:
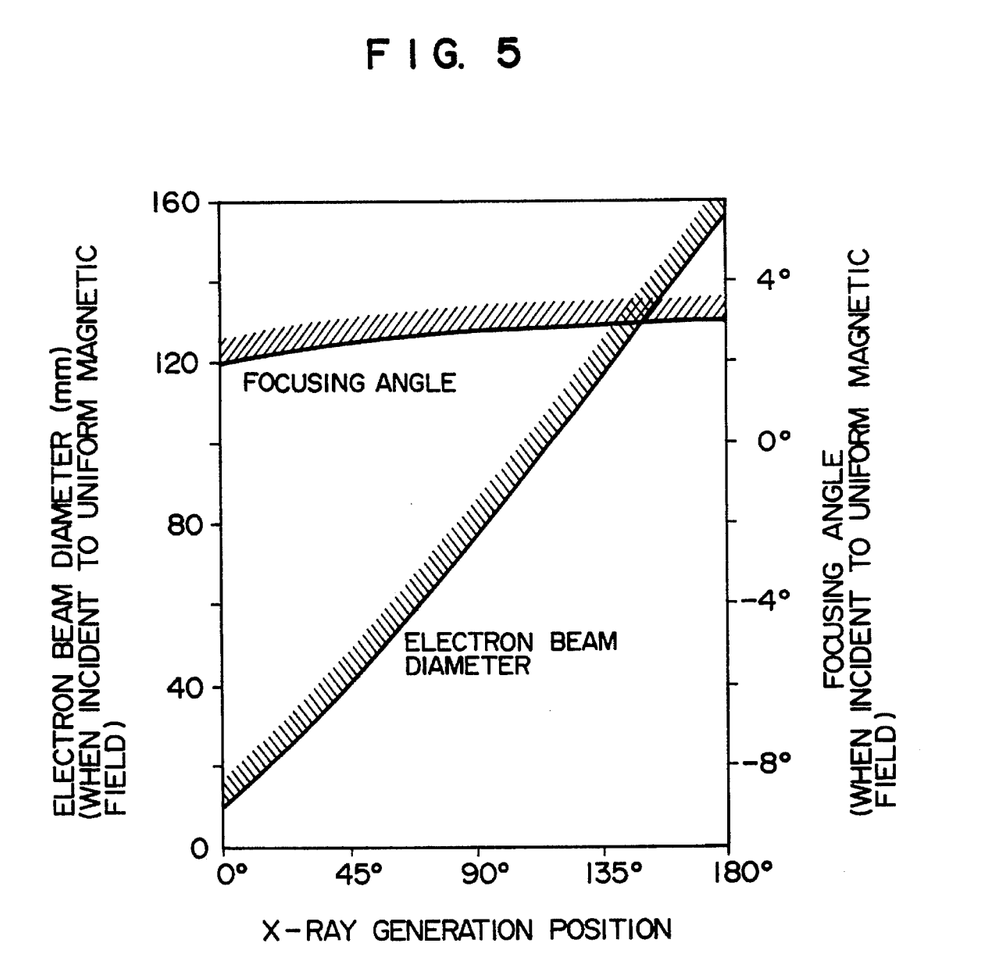
FIG. 5 is a characteristic diagram of the electron beam in a slicing direction in the present invention.

In the embodiment shown in FIGS. 1 and 2, the current value of the electron beam 2 is about 1 A. Therefore, the repulsive force resulting from the space charge effect acting between the electrons cannot be neglected. The electron beam 2 travels while receiving this diverging action and at the same time, receiving also the focusing action due to the magnetic field that is generated by the electron beam itself and the focusing action that is generated due to the arc form deflection of the electron beam 2. As a result, the diameter of the electron beam 2 reaching the anode target 6 changes in accordance with the X-ray generation position. In contrast, scanning must be effected while the diameter of the electron beam on the anode target 6 is kept constant at the minimum possible value in order to attain high resolution of the X-ray CT image in the X-ray CT system. Therefore, the lens system 3 for adjusting the diameter and focusing angle of the electron beam 2 in accordance with the X-ray generation position, when the electron beam 2 is incident into the uniform magnetic field 10, is provided in order to obtain a predetermined diameter of the electron beam 2 on the anode target 6. This lens system 3 comprises a plurality of quadrupole lenses so as to make independent adjustment in the scanning direction, in which the focusing action due to the arc form deflection of the electron beam 2 acts, and in the slicing direction which is substantially orthogonal to the scanning direction and is a direction of the sectional image. FIG. 4 shows the diameter and focusing angle of the electron beam when it is incident into the uniform magnetic field in order to obtain a diameter of the electron beam of about 1 mm in the scanning direction on the anode target 6 over the range of the X-ray generation positions of from 0° to 180°. Here, the X-ray generation position is defined as an angle starting from the center of the arc and embracing the point on the anode target 6 with one of the ends of the anode target 6 being 0°. In this embodiment, the anode target position 62 is set to be the start. FIG. 5 shows a similar diagram in the slicing direction. When the X-ray CT images are taken using the CT system of this embodiment, the images can be obtained at a high speed of at least 20 sheets/second.

Figure 6:
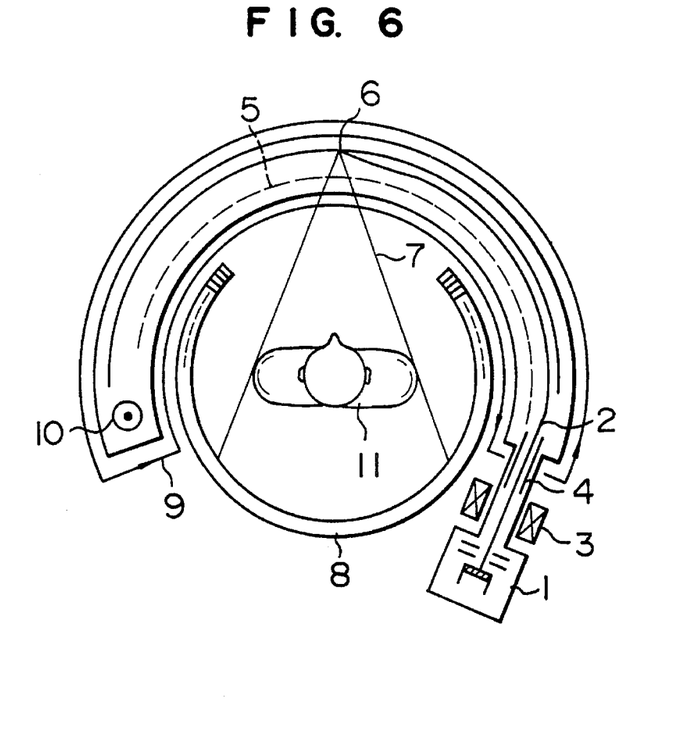
FIG. 6 is a sectional view of the system in accordance with another embodiment of the invention.
Figure 7A:
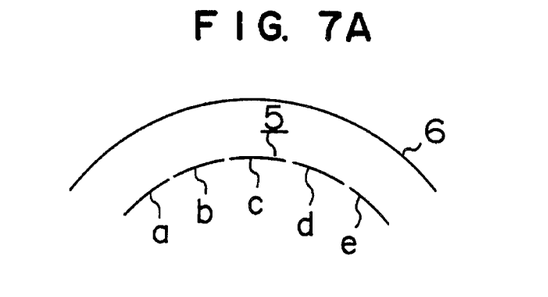
FIG. 7A is a structural view of a deflector in another embodiment of the invention.
Figure 7B:
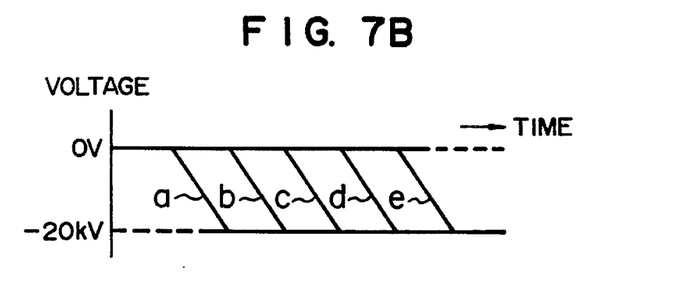
FIG. 7B is a characteristic diagram of the deflector described above.

FIG. 6 is a sectional plan view of the X-ray scanner in the X-ray CT system in accordance with another embodiment of the present invention. In the embodiment shown in FIG. 1, the deflection means to the anode target 6 is of the magnetic field type but it is of an electrostatic type in this embodiment. Furthermore, one magnetic field generation coil having the arc form shown in the drawing is used as a magnetic deflector 9 for arc form deflection. The electrostatic deflector 5 comprises electrostatic deflection plates a, b, c, d, e ... and an applied voltage is 20 kV. The electron beam 2 is deflected by about 60° and irradiates the anode target 6. FIG. 7A is its structural view. The applied voltage to each deflection plate is changed in the form of the teeth of a saw as shown in FIG. 7B so that the electron beam 2 scans continuously on the anode target 6.

Figure 8:
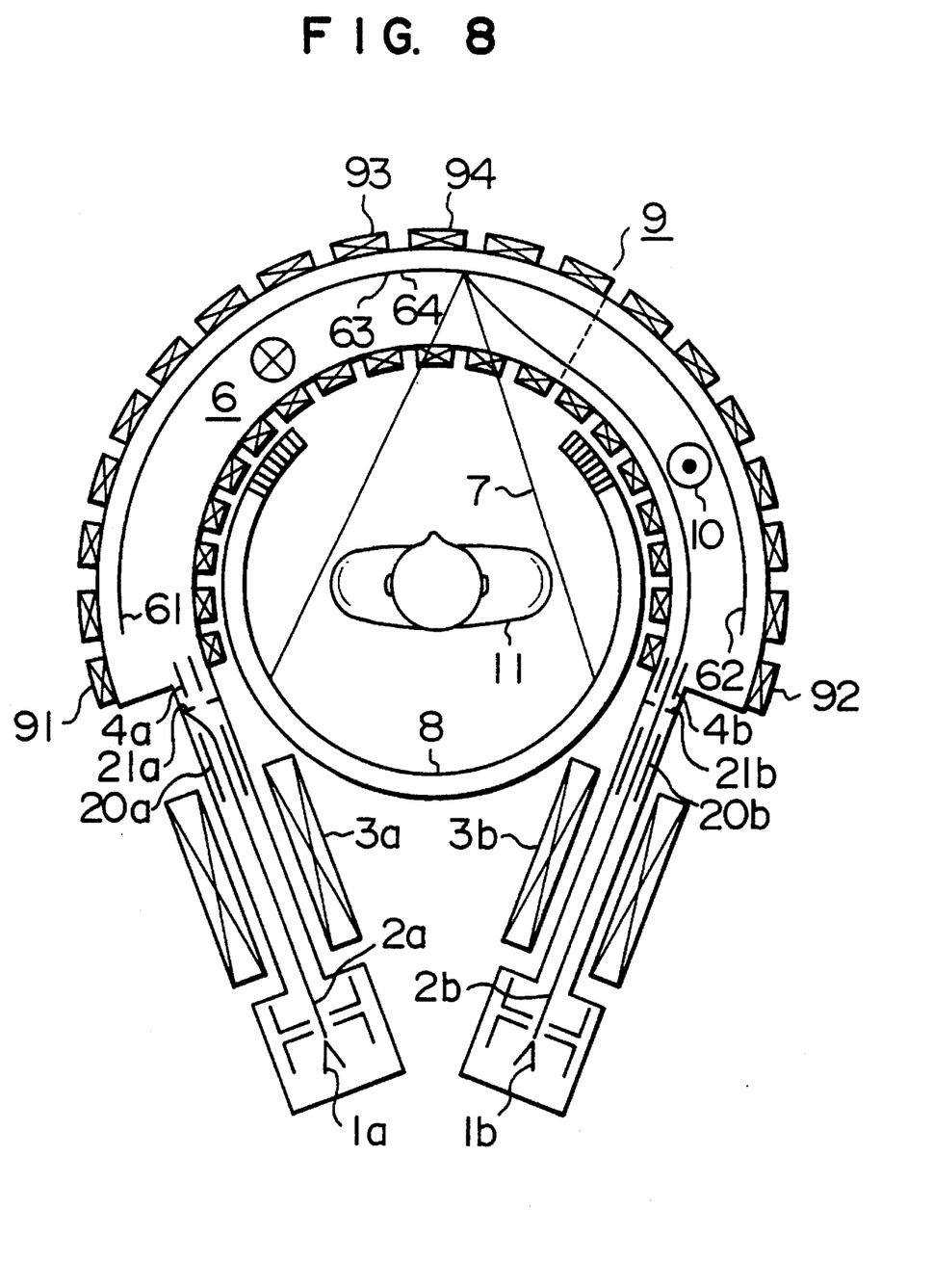
FIG. 8 is a sectional view of the system in accordance with still another embodiment of the invention.

Next, still another embodiment of the present invention, wherein two electron sources are provided, will be explained. FIG. 8 is a sectional plan view showing the X-ray CT system of this embodiment, particularly its X-ray scanner. The electron beam 2a leaving the electron gun 1a as the electron source is focused by the lens system 3a. At this time, the electron beam 2b generated by the electron gun 1b is deflected by a blanking deflector 20b, is irradiated on a diaphragm 21b and is cut off. The electron beam 2a is projected into the uniform magnetic field 10 generated by the magnetic deflector 9 while keeping a desired electron beam diameter and focusing angle, and is deflected in substantially the same way as in the foregoing embodiments. Here, if the magnetic deflector 9 is operated in time sequence from the magnetic deflector 93 to the magnetic deflector 91, the irradiation position of the electron beam 2a on the anode target 6 or in other words, the generation position of the X-ray 7, is scanned, too, from the anode target position 63 to the anode target position 61. Similarly, the anode target from the anode target position 64 to the anode target position 62 is scanned by the electron beam 2b generated by the electron gun 1b and passing through the lens system 3b by operating the magnetic deflector 9 in time sequence from the magnetic deflector 94 to the magnetic deflector 92. At this time, the electron beam 2a generated by the electron gun 1a is cut off likewise by the blanking deflector 20a and the diaphragm 21a.

In FIG. 8, 4a and 4b indicate pipes shielded magnetically.

In this embodiment, the adjustment of the electron beam to focus to about 1 mm in the scanning direction from the X-ray generation positions 0° to 220° by the lens system 3 in substantially in the same way as in FIG. 4 is carried out in the following way. To begin with, the electron beam 2a is irradiated onto the range of 0° to 110° on the anode target 6 and the electron beam 2b is irradiated from 110° to 220°. However, the X-ray generation position in this embodiment is expressed using the anode target position 61 as the start. The diameter of the electron beam at the time of incidence is increased within the range of 40 to 70 mm between 0° and 65°, is decreased within the same range between 65° and 110°; is increased similarly between 110° and 155° and is decreased between 155° and 220°. The diameter of the electron beam in the slicing direction is changed within 100 mm as can be seen from FIG. 5. The focusing angle of each of the electron beams 2a and 2b is changed from −1° to 2° in the scanning direction and from 2° to 3° in the slicing direction. As a result of the adjustment described above, the variation range of the diameter of the electron beam which is adjusted by the lens system 3 is smaller than when only one electron gun is used and the aperture of the lens as well as its dimension in the longitudinal direction are smaller. Accordingly, the apparatus can be made compact in scale.

On the other hand, the operation method different from the one described above may be employed, too. First of all, the electron beam 2a is deflected and after scanning is made from 0° to 45° on the anode target 6, the electron beam 2b is deflected to make scanning from 45° to 115°. Thereafter, scanning is made from 115° to 175° by deflecting the electron beam 2a and from 175° to 220° by deflecting the electron beam 2b. In the mean time, the electron beam which is not used is cut off by the blanking deflector 20a and the diaphragm 21a or by the blanking deflector 20b and the diaphragm 21b. As described above, the complementary operation performed to each other can be accomplished by irradiating the electron beam 2b to the X-ray generation position, at which the electron beam 2a cannot be focused to the target electron beam diameter, and irradiating the electron beam 2a to the X-ray generation position, at which the electron beam 2b cannot be focused to the target electron beam diameter, on the contrary. As a result, the diameter of the electron beam which is smaller than when the electron gun is only one can be obtained on the anode target 6 and high resolution of the X-ray CT image can be accomplished.

Figure 9:
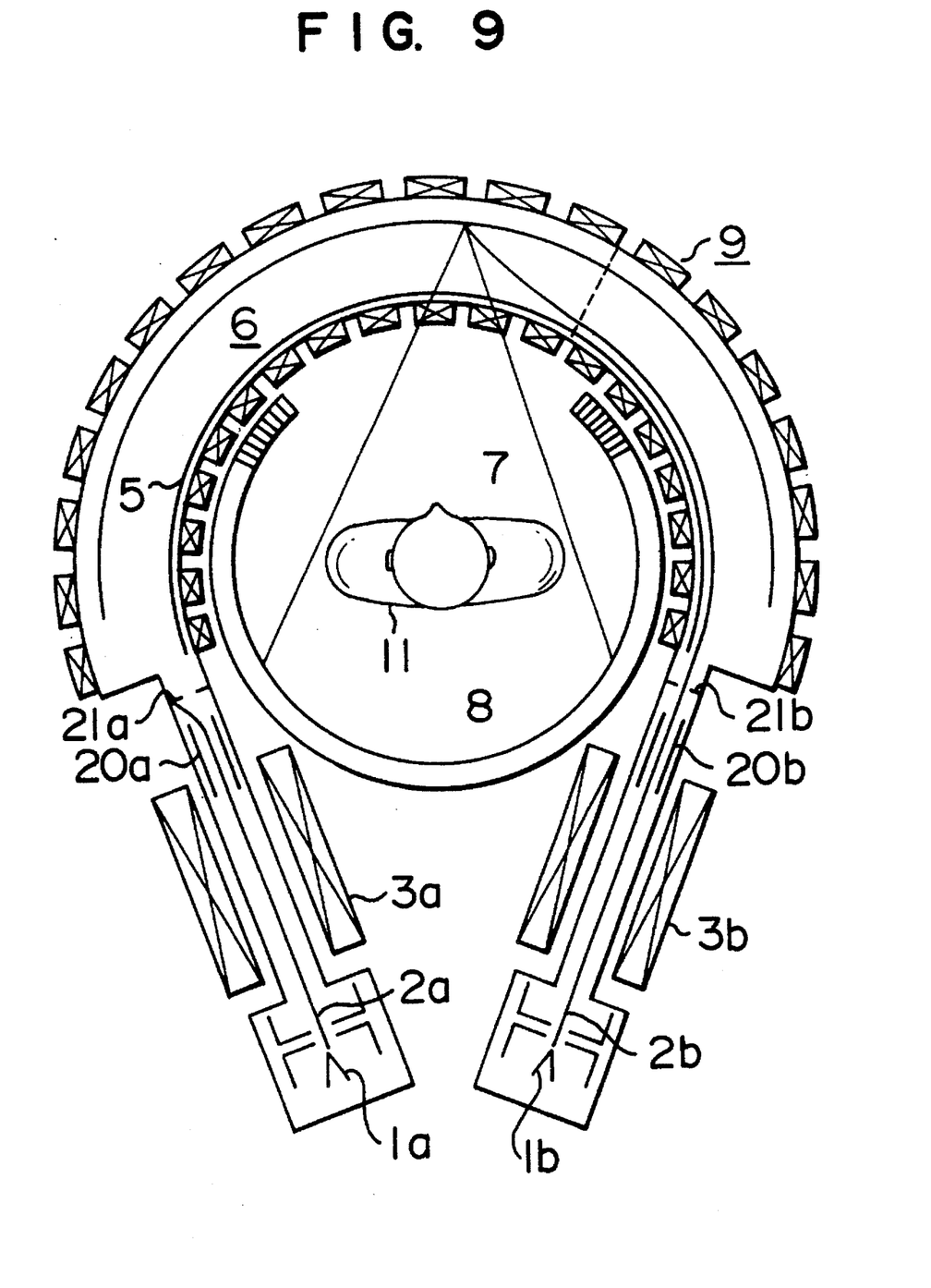
FIG. 9 is a sectional view of the system in accordance with still another embodiment of the invention.

FIG. 9 is a sectional plan view of the X-ray scanner in the X-ray CT system in accordance with still another embodiment of the present invention. In the embodiments shown in FIGS. 1, 2, 6 and 8, the electron beam is deflected to the arc form trajectory by the uniform magnetic field 10, but in this embodiment, it is deflected to the arc form trajectory by the electrostatic field generated by an electrostatic deflector 5. The electrostatic deflector 5 comprises electrode plates shaped in the form of an arc so as to face the anode target 6 while interposing the electron beams 2a and 2b between them. A voltage of about 2 kV is applied to the electrode plate so as to deflect the passing electron beams 2a and 2b. In this case, the magnetic deflector 9 generates only the magnetic field necessary for deflecting the electron beams 2a and 2b outward from the arc form trajectory and causing them to scan on the anode target 6. It is also possible to delete the magnetic deflector 9, to arrange a plurality of electrostatic deflectors by dividing the electrostatic deflector 5 and to perform both deflection of the electron beams 2a and 2b and scanning on the anode target 6 by controlling the resulting electrostatic field.

Figure 10:
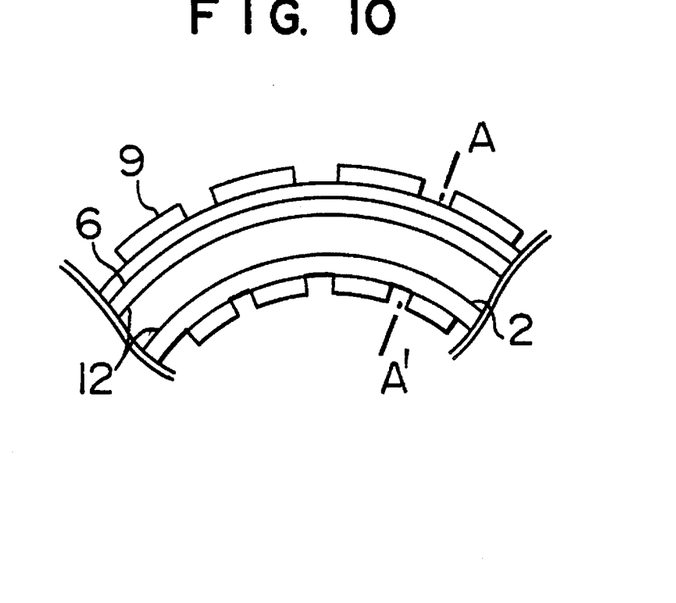
FIG. 10 is a partial sectional view showing a magnetic field generation mechanism for focusing an electron beam in the present invention.
Figure 11:
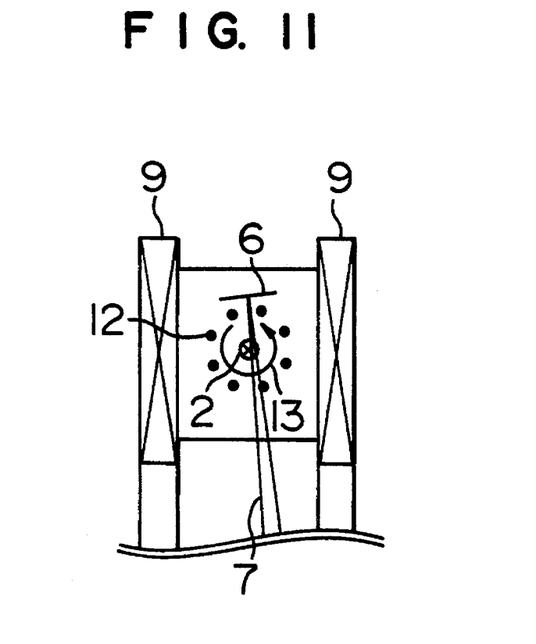
FIG. 11 is a sectional view taken along line A—A' in FIG. 10.
Figure 12:
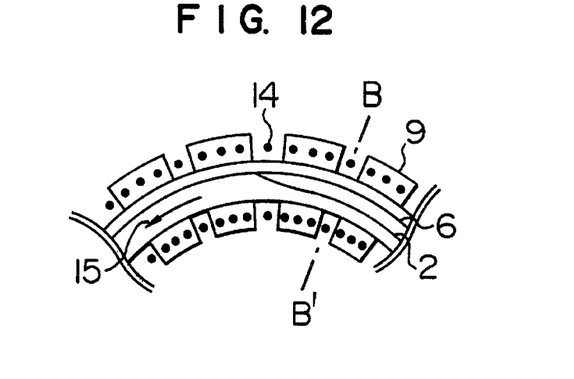
FIG. 12 is a partial sectional view showing a magnetic field generation mechanism for focusing an electron beam in the present invention.
Figure 13:
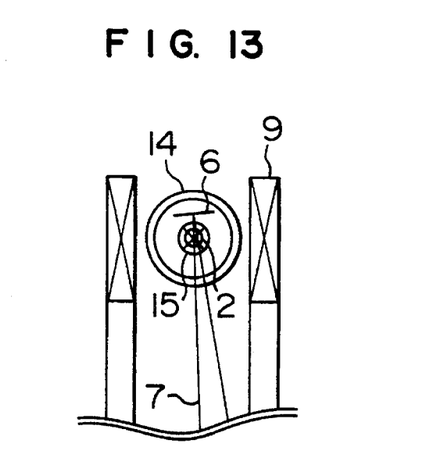
FIG. 13 is a sectional view taken along line B—B' in FIG. 12.

FIGS. 10 and 11 and FIGS. 12 and 13 show the constructions of the X-ray CT system in accordance with other embodiments of the present invention. FIGS. 10 and 12 are plan view of the X-ray scanner part, FIG. 11 is a sectional view taken along line A—A' of FIG. 10 and FIG. 13 is a sectional view taken along line B—B' of FIG. 12. These embodiments have a focusing magnetic field generation mechanism for preventing the divergence of the electron beam 2 due to the space charge effect.

The most critical problem encountered when constituting the X-ray source by scanning the electron beam is divergence of the electron beam. The magnetic field generated by the electron beam applies the focusing action on the electron beam but in the case of an accelerating voltage of 120 kV, its focusing force is about one-third of the diverging force due to the space charge effect. Accordingly, the focusing force corresponding to the remaining two-thirds must be provided by an external magnetic field. There are two kinds of magnetic fields which provide this focusing force. One is a rotating magnetic field inside a plane perpendicular to the travelling direction of the electron beam, and the other is a magnetic field in parallel with the travelling direction of the electron beam. The former focuses merely the electron beam and the latter focuses the electron beam with rotation.

First of all, in the embodiment shown in FIGS. 10 and 11, a plurality of wires 12 are disposed on the circumference having the electron beam 2 as its center in parallel with the travelling direction of the electron beam 2. A current is caused to flow through these wires 12 in a direction opposite to the travelling direction of the electron beam 2. In other words, a magnetic field 13 in the rotating direction is generated inside the plane perpendicular to the electron beam 2. This rotating magnetic field 13 prevents the divergence of the electron beam 2 due to the space charge effect. The wires 12 for generating the focusing magnetic field in this embodiment are eight wires disposed on the circumference having an inner diameter of 30 mm, and a maximum 2 A of current is caused to flow through each wire 12 so as to prevent the divergence of the electron beam 2. Accordingly, the diameter of the electron beam 2 of about 1 mm for irradiating the anode target 6 can be accomplished. At this time, the beam diameter of the electron beam 2 in its arc form trajectory is always constant, and hence the diameter of the electron beam 2 that irradiates the anode target 6 from the anode target position 61 to the anode target position 62 is constant as well. Though the anode target 6 is disposed outside the wires 12 in this embodiment, it may be disposed inside the wires 12. The number of the wires described herein is merely illustrative and is in no way limitative of the present invention.

FIGS. 12 and 13 show another embodiment for preventing the divergence of the electron beam 2. A solenoid coil 14 is disposed in the travelling direction of the electron beam 2 in such a manner as to encompass the electron beam 2. This coil 14 generates a magnetic field 15 in parallel with the travelling direction of the electron beam 2 and applies the focusing action to the electron beam 2.

As described above, FIGS. 10 to 13 illustrate the embodiments which prevent the divergence of the electron beam due to the space charge effect. In short, any structure may be employed so long as it applies a focusing action to the electron beam. For example, a quadrupole lens structure can be employed. Though the magnets in the foregoing embodiments are all electromagnets, a similar focusing magnetic field can be generated by use of permanent magnets, and the gist of the present invention is not at all deteriorated by such a structure.

Figure 14:
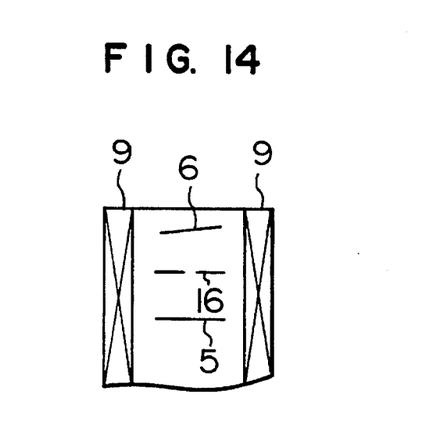
FIG. 14 is a partial sectional view of the system in accordance with still another embodiment of the invention.

FIG. 14 shows the construction of the X-ray CT system in accordance with still another embodiment of the present invention and is a partial sectional view of its X-ray scanner. This embodiment is the same as the electrostatic deflection type shown, for example, in FIG. 6. Particularly, the electron beam 2 is derived from the electron gun 1 at a low accelerating voltage of 20 kV and is deflected by the deflector 5, and there is provided an electrode 16 for the purpose of post-deflection acceleration of the electron beam 2 by a 100 kV voltage applied to the anode target 6. Accordingly, energy of the electron beam irradiating the anode target 6 is the same as in the other embodiments. In this case, the magnetic field produced by the magnetic field generation coil 9 is about 9.6 Gauss, the applied voltage of the deflector 5 is about 3 kV, and the operations can be carried out in the same way as in the first embodiment. The electrode 16 (which is at the ground level potential in this embodiment) has a slit-like shape and the electron beam 2 can be focused more finely than in the first embodiment by the lens action occurring between the electrode 16 and the anode target 6.

Figure 15A:
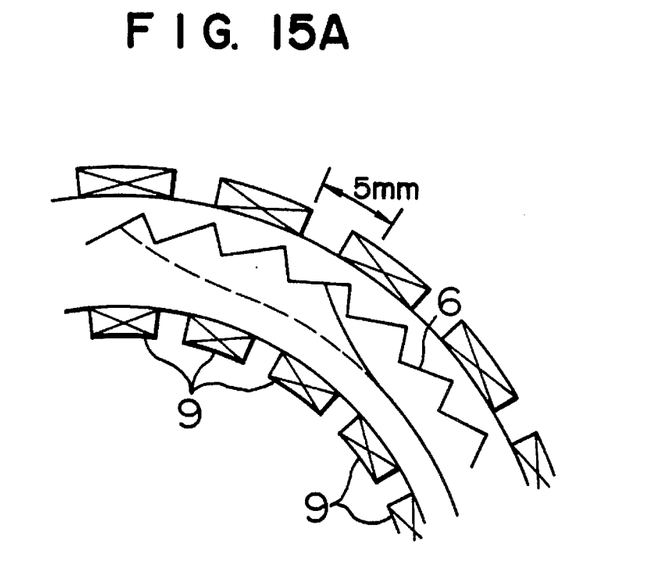
FIGS. 15A and 15B are partial sectional views each showing the system in accordance with still another embodiment of the invention.
Figure 15B:
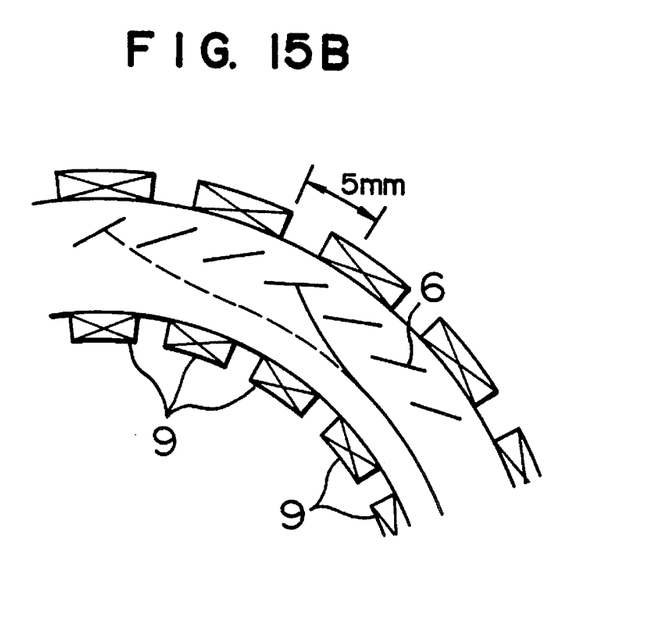

FIG. 15A is a plan view of the X-ray scanner part in the X-ray CT system in accordance with still another embodiment of the present invention. The anode target 6 which has the shape of the side surface of a circular truncated cone in the embodiments shown in FIGS. 1, 6, 8 and 9 is replaced by an anode target 6 which has concavo-convexities of the shape of the teeth of a saw in the circumferential direction as shown in FIG. 15A in this embodiment. The mean radius of the anode target 6 is set to 60 cm and the angular gap between the X-ray generation positions is set to 0.5°. Accordingly, the concavo-convexities are defined with gaps of about 5 mm. In accordance with this embodiment, the dimension of the effective focus of the X-rays 7 generated from the anode target 6 is reduced and high resolution can be accomplished. This anode target 6 can be constituted by a plurality of intermittent anode targets 6 while leaving only the irradiation surface of the electron beam 2 as shown in FIG. 15B. An arc form anode target 6 as shown, for example, in FIGS. 1, 6, 8 and 9, can of course be constituted intermittently.

The description given above explains some preferred embodiments of the present invention. In short, the present invention adjusts the diameter and focusing angle of the electron beam emitted from the electron source in accordance with the X-ray generation position, deflects the electron beam to the arc form trajectory inside the same plane as the anode target 6 having the arc shape to let it scan on the anode target 6, detects the resulting X-rays with the detector 8 arranged to face the anode target 6 and obtains the signals so as to obtain the X-ray CT image. It is therefore possible, for example, to blank of the electron beam and to pulse it in synchronism with sampling for the signal detection time, and to perform scanning of the anode target every 0.5°. The anode target 6 is disposed outside the arc form trajectory of the electron beam and uses the reflected X-rays, but it is also possible to obtain the X-ray CT image by the transmitted X-rays by disposing the thin anode target 6 inside the arc form trajectory. The electron gun is not particularly limited to LaB$_6$ (lanthanum hexaboride) and the number of the electron guns is not limited to one or two, either. Lens means for focusing the electron beam immediately before it is irradiated to the anode target 6 inside the deflection system may be employed in place of the lens system 3 for adjusting the diameter of the electron beam and its focusing angle when incident to uniform magnetic field 10, and such a lens means may be combined with the lens system 3 described above in order to make adjustment by using both of them. In short, what is required is the means for adjusting the electron beam so that the diameter of the electron beam to be irradiated onto the anode target 6 remains constant irrespective of the X-ray generation position, and moreover the diameter assumes the smallest possible value. An astigmatism corrector and an axis adjuster for the electron beam do not render any problem to the gist of the present invention even when they are provided. Furthermore, it will be obvious that the dimensions and performance of the embodiments given above are merely illustrative and the present invention can be practiced without being limited to them.

In accordance with the present invention, the electron beam can be deflected inside substantially the same plane as the anode target for generating the X-ray and the detector, and a predetermined small electron beam diameter can be obtained on the anode target. Accordingly, the present invention can provide an X-ray CT system which is compact in scale and can obtain an X-ray CT image having high resolution at a high speed.

What is claimed is:

1. An X-ray computed tomography system comprising:
   a reflection-type anode target for an X-ray source disposed in the form of an arc;
   a plurality of X-ray detectors disposed in such a manner as to face said anode target;
   an electron source for generating an electron beam for scanning said anode target in the form of an arc so as to enable generation of X-rays from different positions on said anode target;
   first deflection means for deflecting a trajectory of said electron beam to an arc form trajectory in a plane inclusive of said anode target;
   second deflection means for causing said electron beam to scan said anode target in the form of an arc in said plane inclusive of said anode target, thereby causing X-rays to be generated by said anode target; and
   lens means for adjusting said electron beam in accordance with an X-ray generation position on said anode target.

2. An X-ray computed tomography system according to claim 1, wherein said lens means comprises multi-stage quadrupole lenses.

3. An X-ray computed tomography system comprising:
   a reflection-type anode target for an X-ray source disposed in the form of an arc;
   a plurality of X-ray detectors disposed in such a manner as to face said anode target;
   an electron source for generating an electron beam for scanning said anode target in the form of an arc;
   first deflection means for deflecting a trajectory of said electron beam to an arc form trajectory in a plane inclusive of said anode target;
   second deflection means for causing said electron beam to scan said anode target in the form of an arc in said plane inclusive of said anode target, thereby causing X-rays to be generated by said anode target; and
   lens means for adjusting said electron beam;
   wherein said lens means adjusts a diameter and a focusing angle of said electron beam in accordance with an X-ray generation position on said anode target.

4. An X-ray computed tomography system according to claim 1, wherein said lens means is constituted in such a fashion that it can adjust a diameter and a focusing angle of said electron beam independently in a plane inclusive of said arc form trajectory of said electron beam and in a direction crossing said plane substantially at right angles.

5. An X-ray computed tomography system according to claim 1, wherein said first deflection means comprises one or a plurality of magnetic deflectors.

6. An X-ray computed tomography system according to claim 1, wherein said first deflection means comprises one or a plurality of electrostatic deflectors.

7. An X-ray computed tomography system according to claim 1, wherein said second deflection means comprises a magnetic deflector.

8. An X-ray computed tomography system according to claim 1, wherein said second deflection means comprises an electrostatic deflector.

9. An X-ray computed tomography system according to claim 1, wherein said first deflection means and said second deflection means comprise the same deflection means.

10. An X-ray computed tomography system according to claim 1, wherein said plurality of detectors have an angle range greater than that of said anode target and a difference between the angle ranges is substantially equal to the broadening angle of the X-rays generated by said anode target.

11. An X-ray computed tomography system according to claim 1, wherein said anode target is disposed in the form of an arc within the range of at least 180° and said plurality of detectors are disposed in the form of an arc within the range of at least 220°.

12. An X-ray computed tomography system according to claim 1, wherein said electron beam is a pulsed electron beam.

13. An X-ray computed tomography system according to claim 1, wherein said anode target has concavo-convexities of the shape of the teeth of a saw in the form of an arc in the circumferential direction.

14. An X-ray computed tomography system according to claim 1, wherein said electron source comprises at least two electron sources.

15. An X-ray computed tomography system according to claim 1, wherein an energy of said electron beam deflected to the arc form trajectory by said first deflection means is set to a lower value than an energy of said electron beam irradiating said anode target.

16. An X-ray computed tomography system according to claim 1, wherein said first deflection means includes focusing means for focusing said electron beam when said electron beam is deflected to said arc form trajectory.

17. An X-ray computed tomography system comprising:
   a reflection-type anode target for an X-ray source disposed in the form of an arc;
   a plurality of X-ray detectors disposed in such a manner as to face said anode target;
   at least two electron sources for generating an electron beam for scanning said anode target in the form of an arc;
   deflection means for deflecting a trajectory of said electron beam to an arc form trajectory in a plane inclusive of said anode target and causing said electron beam to scan said anode target in the form of an arc in said plane inclusive of said anode target, thereby causing X-rays to be generated by said anode target; and lens means for adjusting a diameter and a focusing angle of said electron beam in accordance with an X-ray generation position on said anode target.

18. An X-ray computed tomography system according to claim 17, wherein an energy of said electron beam deflected to the arc form trajectory by said deflection means is set to a lower value than an energy of said electron beam irradiating said anode target.

19. An X-ray computed tomography system comprising:

a reflection-type anode target for an X-ray source disposed in the form of an arc;

a plurality of X-ray detectors disposed in such a manner as to face said anode target;

an electron source for generating an electron beam for scanning said anode target in the form of an arc;

deflection means for deflecting a trajectory of said electron beam to an arc form trajectory in a plane inclusive of said anode target and causing said electron beam to scan said anode target in the form of an arc in said plane inclusive of said anode target, thereby causing X-rays to be generated by said anode target; and focusing means for focusing said electron beam when said electron beam is deflected to said arc form trajectory so as to provide a substantially constant diameter electron beam independent of position along said arc form trajectory.

20. An X-ray computed tomography system according to claim 19, wherein said focusing means comprises magnetic field generation means for generating a magnetic field in parallel with the travelling direction of said electron beam.

21. An X-ray computed tomography system according to claim 19, wherein said focusing means comprises magnetic field generation means for generating a rotating magnetic field in a plane perpendicular to a travelling direction of said electron beam.

22. A method of X-ray computed tomography comprising the steps of:

adjusting a diameter and a focusing angle of an electron beam to desired values in accordance with a predetermined position on a reflection-type anode target for an X-ray source disposed in a plane when said electron beam is deflected in an arc in said plane and is irradiated to said anode target at said predetermined position, thereby causing X-rays to be generated by said anode target;

irradiating the X-rays generated by said anode target to an object the image of which is to be taken;

detecting the irradiated X-rays after transmission through said object; and imaging a section of said object based on the detected X-rays and displaying the resulting image.

23. An X-ray scanner for an X-ray computed tomography system, comprising:

a reflection-type anode target for an X-ray source disposed in the form of an arc in a plane;

an electron source disposed in the same plane as said anode target;

means for scanning an electron beam from said electron source in an arc along said anode target, thereby causing X-rays to be generated by said anode target, said arc in which said electron beam is scanned being in said plane in which said anode target is disposed in the form of an arc;

a plurality of X-ray detectors disposed in such a manner as to face said anode target; and lens means for adjusting a diameter and a focusing angle of said electron beam in accordance with an X-ray generation position on said anode target.

24. An X-ray scanner for an X-ray computed tomography system according to claim 23, wherein said plurality of detectors are disposed in a plane near and substantially parallel to said plane in which said anode target is disposed in the form of an arc.

25. An X-ray scanner for an X-ray computed tomography system according to claim 23, wherein said means for scanning includes means for focusing said electron beam.

26. An X-ray computed tomography system according to claim 1, wherein said lens means is disposed between said electron source and said first deflection means.

27. An X-ray computed tomography system according to claim 1, further comprising means for correcting deflection directions of said electron beam between said electron source and said first deflection means.

28. An X-ray computed tomography system according to claim 1, further comprising shielding means disposed between said electron source and said first deflection means for establishing a field-free region through which said electron beam passes prior to entering said first deflection means.

29. An X-ray computed tomography system according to claim 17, further comprising shielding means disposed between said electron source and said deflection means for establishing a field-free region through which said electron beam passes prior to entering said deflection means.

30. An X-ray computed tomography system according to claim 19, further comprising shielding means disposed between said electron source and said deflection means for establishing a field-free region through which said electron beam passes prior to entering said deflection means.

31. An X-ray computed tomography method according to claim 22, further comprising the step of establishing a field-free region through which said electron beam passes prior to being deflected.

32. An X-ray scanner for an X-ray computed tomography system according to claim 23, further comprising shielding means disposed between said electron source and said scanning means for establishing a field-free region through which said electron beam passes prior to entering said scanning means.

* * * * *